US010750988B2

(12) United States Patent
Fujii et al.

(10) Patent No.: US 10,750,988 B2
(45) Date of Patent: Aug. 25, 2020

(54) FATIGUE DEGREE DETERMINATION DEVICE, AND FATIGUE DEGREE DETERMINATION METHOD

(71) Applicants: OMRON HEALTHCARE Co., Ltd., Kyoto (JP); OSAKA CITY UNIVERSITY, Osaka (JP)

(72) Inventors: Kenji Fujii, Kyoto (JP); Shingo Yamashita, Kyoto (JP); Yasuyoshi Watanabe, Osaka (JP); Kei Mizuno, Osaka (JP)

(73) Assignees: OMRON HEALTHCARE Co., Ltd., Kyoto (JP); OSAKA CITY UNIVERSITY, Osaka (JP)

( * ) Notice: Subject to any disclaimer, the term of this patent is extended or adjusted under 35 U.S.C. 154(b) by 84 days.

(21) Appl. No.: 16/270,794

(22) Filed: Feb. 8, 2019

(65) Prior Publication Data
US 2019/0167173 A1 Jun. 6, 2019

Related U.S. Application Data

(63) Continuation of application No. PCT/JP2017/026567, filed on Jul. 21, 2017.

(30) Foreign Application Priority Data
Aug. 12, 2016 (JP) .................. 2016-158676

(51) Int. Cl.
*A61B 5/00* (2006.01)
*A61B 5/16* (2006.01)
(Continued)

(52) U.S. Cl.
CPC .............. *A61B 5/165* (2013.01); *A61B 5/024* (2013.01); *A61B 5/0245* (2013.01); *A61B 5/16* (2013.01);
(Continued)

(58) Field of Classification Search
CPC .......... A61B 5/024; A61B 5/0245; A61B 5/16; A61B 5/165; A61B 5/4806; A61B 5/681; A61B 5/7278
See application file for complete search history.

(56) References Cited

U.S. PATENT DOCUMENTS

2004/0046666 A1 3/2004 Yasuchi
2015/0150516 A1 6/2015 Tochikubo et al.
(Continued)

FOREIGN PATENT DOCUMENTS

JP 2004-081723 A 3/2004
JP 2014-050451 A 3/2014
(Continued)

OTHER PUBLICATIONS

Office Action dated Dec. 3, 2019, in corresponding Japanese Application No. 2016-158676; 5 pages.
(Continued)

*Primary Examiner* — George Manuel
(74) *Attorney, Agent, or Firm* — Maier & Maier, PLLC

(57) ABSTRACT

A fatigue degree determination device includes a fatigue degree determination unit. A first biological heart rate is acquired while a user is awake and at rest, based on a biological heart rate measured from the user. A second biological heart rate is acquired while the user is sleeping, based on the biological heart rate measured from the user. The fatigue degree determination unit determines a fatigue degree of the user, based on information read out from a storage medium, the first biological heart rate and the second biological heart rate. The storage medium stores the information in which a degree of change of one biological heart rate relative to the other biological heart rate of a biological heart rate while a person is awake and at rest and a biological (Continued)

heart rate while the person is sleeping and a fatigue degree are associated with each other.

11 Claims, 7 Drawing Sheets

(51) Int. Cl.
*A61B 5/0245* (2006.01)
*A61B 5/024* (2006.01)

(52) U.S. Cl.
CPC ............ *A61B 5/4806* (2013.01); *A61B 5/681* (2013.01); *A61B 5/7278* (2013.01)

(56) References Cited

U.S. PATENT DOCUMENTS

2016/0270718 A1* 9/2016 Heneghan .............. G16H 50/30
2017/0035365 A1   2/2017 Hasegawa et al.

FOREIGN PATENT DOCUMENTS

| JP | 2015-109888 A | 6/2015 |
| JP | 2015-173684 A | 10/2015 |
| JP | 2015-195982 A | 11/2015 |
| JP | 2015-229068 A | 12/2015 |

OTHER PUBLICATIONS

International Search Report with English translation and Written Opinion dated Oct. 17, 2017 in corresponding International Application No. PCT/JP2017/026567; 8 pages.

* cited by examiner

FATIGUE DEGREE DETERMINATION DEVICE, AND FATIGUE DEGREE DETERMINATION METHOD

CROSS REFERENCE TO RELATED APPLICATIONS

This application is a continuation of PCT application No. PCT/JP2017/026567, which was filed on Jul. 21, 2017 based on Japanese Patent Application (No. 2016-158676) filed on Aug. 12, 2016, the contents of which are incorporated herein by reference.

FIELD

The present invention relates to a fatigue degree determination device, a fatigue degree determination method, a fatigue degree determination program and a biological information measurement device.

BACKGROUND

A device or system configured to provide information about user's health and the like on the basis of biological information measured from a user has been known (refer to Patent Documents 1 to 3).

Patent Document 1 discloses a system configured to evaluate user's chronic fatigue on the basis of a user's heartbeat interval. The system is configured to perform frequency analysis of the heartbeat interval while the user is sleeping, and to determine whether or not the chronic fatigue on the basis of a result of the frequency analysis.

Patent Document 2 discloses a wearable device configured to obtain stress information of a user on the basis of a heart rate of the user who is in a deep sleep state.

Patent Document 3 discloses a device that, when a user's biological heart rate measured at any timing is lowered by a threshold value or greater with respect to biological heart rate data while the user is awake, which is stored in advance, determines that the user is fatigued, asleep or fatigued and asleep, and when a difference between the user's biological heart rate measured at any timing and biological heart rate data while the user is sleeping, which is stored in advance, is smaller than a threshold value, determines that the user is fatigued, asleep or fatigued and asleep.

Patent Document 1: JP-A-2015-109888
Patent Document 2: JP-A-2015-173684
Patent Document 3: JP-A-2015-195982

SUMMARY

A fatigue degree determination device of the present invention includes a first biological heart rate acquisition unit configured to acquire a first biological heart rate while a user is awake and at rest, based on a biological heart rate measured from the user, a second biological heart rate acquisition unit configured to acquire a second biological heart rate while the user is sleeping, based on the biological heart rate measured from the user, and a fatigue degree determination unit configured to determine a fatigue degree of the user, based on information read out from a storage medium and the first biological heart rate and second biological heart rate, the storage medium storing the information in which a degree of change of one biological heart rate relative to the other biological heart rate of a biological heart rate while a person is awake and at rest and a biological heart rate while the person is sleeping and a fatigue degree are associated with each other.

A fatigue degree determination method of the present invention includes a first biological heart rate acquisition step of acquiring a first biological heart rate while a user is awake and at rest, based on a biological heart rate measured from the user, a second biological heart rate acquisition step of acquiring a second biological heart rate while the user is sleeping, based on the biological heart rate measured from the user, and a fatigue degree determination step of determining a fatigue degree of the user, based on information read out from a storage medium and the first biological heart rate and second biological heart rate, the storage medium storing the information in which a degree of change of one biological heart rate relative to the other biological heart rate of a biological heart rate while a person is awake and at rest and a biological heart rate while the person is sleeping and a fatigue degree are associated with each other.

A fatigue degree determination program of the present invention is configured to enable a computer to execute a first biological heart rate acquisition step of acquiring a first biological heart rate while a user is awake and at rest, based on a biological heart rate measured from the user, a second biological heart rate acquisition step of acquiring a second biological heart rate while the user is sleeping, based on the biological heart rate measured from the user, and a fatigue degree determination step of determining a fatigue degree of the user, based on information read out from a storage medium and the first biological heart rate and second biological heart rate, the storage medium storing the information in which a degree of change of one biological heart rate relative to the other biological heart rate of a biological heart rate while a person is awake and at rest and a biological heart rate while the person is sleeping and a fatigue degree are associated with each other.

A biological information measurement device of the present invention includes the fatigue degree determination device and a measurement unit configured to measure a biological heart rate from the user, wherein the first biological heart rate acquisition unit is configured to acquire the first biological heart rate by generating the first biological heart rate from the biological heart rate measured by the measurement unit, and wherein the second biological heart rate acquisition unit is configured to acquire the second biological heart rate by generating the second biological heart rate from the biological heart rate measured by the measurement unit.

DETAILED DESCRIPTION

The device disclosed in Patent Document 3 can determine whether the user is fatigued or not but cannot determine a degree of the fatigue (fatigue degree).

The wearable device disclosed in Patent Document 2 is configured to obtain, as an index for evaluating the stress, an integrated value of times in which the heart rate measured from the user is equal to or larger than a value obtained by multiplying the heart rate in the deep sleep state by a stress coefficient.

In the above method, since a magnitude of the index is varied by the time in which the heart rate is measured, it is difficult to accurately evaluate the stress.

According to the system disclosed in Patent Document 1, since it is necessary to perform the complex calculation processing referred to as the frequency analysis of the heartbeat interval, the processing load for determining a degree of the chronic fatigue increases.

The present invention has been made in view of the above situations, and an object thereof is to provide a fatigue degree determination device, a fatigue degree determination method, a fatigue degree determination program and a biological information measurement device capable of accurately obtaining a fatigue degree under light load.

Hereinafter, an illustrative embodiment of the present invention will be described with reference to the drawings.

Figure 1:
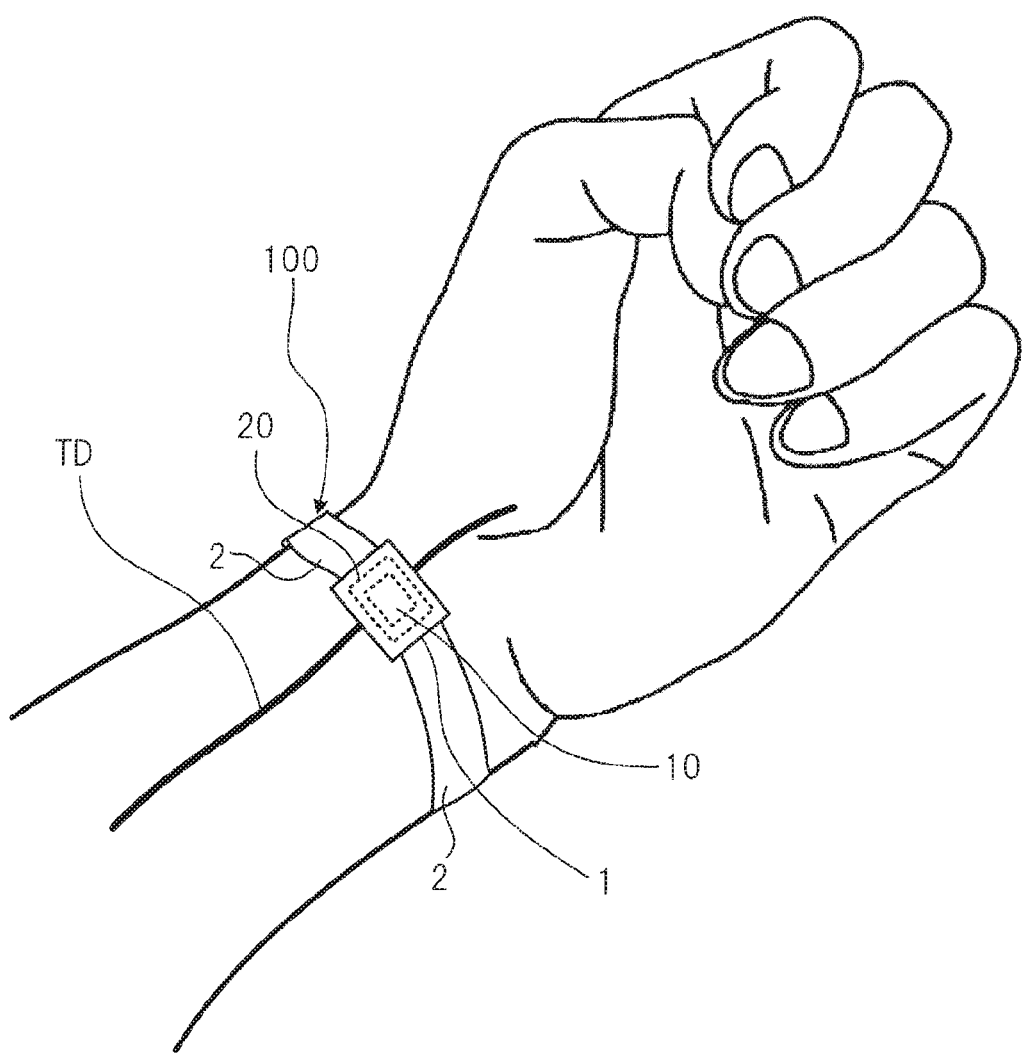
FIG. 1 is a pictorial view depicting a schematic configuration of an outer shape of a biological information measurement device 100 for illustrating an illustrative embodiment of the present invention.

FIG. 1 is a pictorial view depicting a schematic configuration of an outer shape of a biological information measurement device 100 for illustrating an illustrative embodiment of the present invention. The biological information measurement device 100 is used with being worn on a user's wrist.

The biological information measurement device 100 includes a main body part 1 and a belt 2 fixed to the main body part 1. The biological information measurement device 100 is used with being worn on the wrist having skin under which the radial artery TD, which is a pulse wave detection target, exists, and is used with the main body part 1 being worn on the wrist by the belt 2.

The biological information that is to be measured by the biological information measurement device 100 includes blood pressure information such as a systolic arterial pressure, a diastolic pressure, a pulse pressure and the like, pulse information such as a pulse rate and the like, heartbeat information such as a heart rate and the like, and the like. The pulse rate and the heart rate indicate the number of times of beat of a heart or the number of times conforming to the same, and are collectively referred to as 'biological heart rate' in the specification. In the below, the biological information measurement device 100 measures a pulse rate, as the biological heart rate.

In the meantime, the heart rate is the number of times of beat of a heart, and the pulse rate indicates the number of times that the artery beats as a pressure generated by the blood pumped from the heart by the beat of the heart is transferred to the peripheral blood vessel. Usually, the pulse rate and the heart rate of the healthy person are the same. Therefore, in the specification, the pulse rate is treated to be synonymous with the heart rate.

The main body part 1 of the biological information measurement device 100 includes a pressure sensor 10 for detecting a pressure pulse wave from the radial artery TD and a pressing mechanism 20 for pressing the pressure sensor 10 to the wrist.

Figure 2:
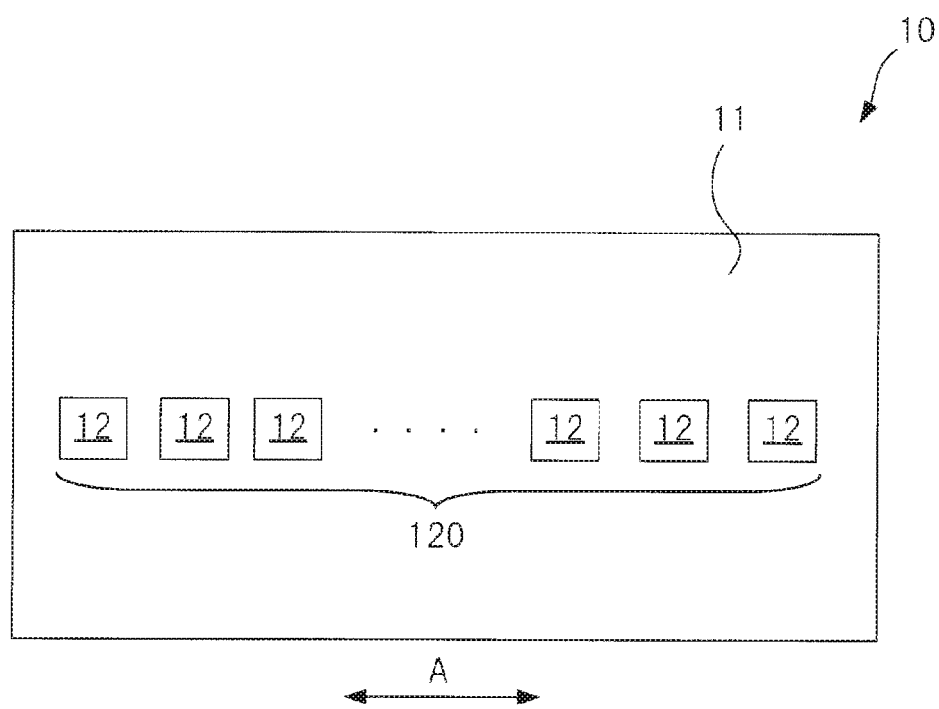
FIG. 2 is a pictorial plan view of a pressure sensor 10 of the biological information measurement device 100 shown in FIG. 1, as seen from a contact surface-side with a wrist.

FIG. 2 is a pictorial plan view of the pressure sensor 10 of the biological information measurement device 100 shown in FIG. 1, as seen from a contact surface-side with the wrist. As shown in FIG. 2, the pressure sensor 10 has an element row 120 formed on a base member 11 having a flat plate shape.

The element row 120 is configured by a plurality of pressure detecting elements 12 aligned side by side in a direction A, which is one direction. As the pressure detecting element 12, an element configured to detect a pressure and to convert the same into an electric signal, for example, an element using a piezo resistance effect may be used.

An interval of the plurality of pressure detecting elements 12 in the aligning direction is set to be sufficiently small so that the required and sufficient number of the elements can be disposed above the radial artery TD. A distance between the pressure detecting elements, which are disposed at both end portions, of the plurality of pressure detecting elements 12 is set to be sufficiently larger than a diameter size of the radial artery TD.

The pressure sensor 10 is pressed to the wrist by the pressing mechanism 20 in a state where the direction A, which is the aligning direction of the plurality of pressure detecting elements 12 included in the element row 120, intersects with an extending direction of the radial artery TD. In the meantime, the pressure sensor 10 may have a configuration where a plurality of element rows 120 is aligned in a direction perpendicular to the direction A on the base member 11.

Figure 3:
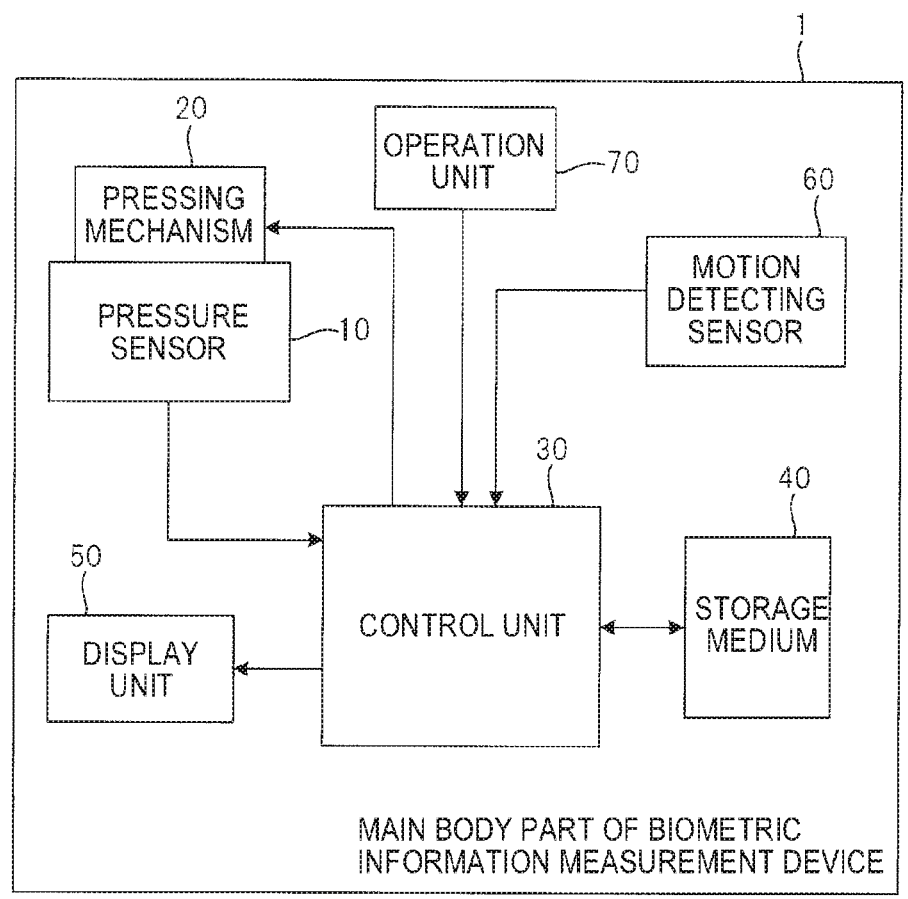
FIG. 3 depicts an internal hardware configuration of a main body part 1 of the biological information measurement device 100 shown in FIG. 1.

FIG. 3 depicts an internal hardware configuration of the main body part 1 of the biological information measurement device 100 shown in FIG. 1.

The main body part 1 includes the pressure sensor 10, the pressing mechanism 20, a control unit 30 configured to collectively control the entire main body part, a storage medium 40, a display unit 50, a motion detecting sensor 60, and an operation unit 70.

The pressing mechanism 20 is configured by an air bag fixed to an opposite surface to a surface of the base member 11 on which the element row 120 is formed, and a pump for adjusting an internal pressure of the air bag. A pressing force (internal pressure of the pump), which is to be applied to the wrist by the pressing mechanism 20, is controlled by the control unit 30.

As the pressing mechanism 20, any mechanism capable of pressing the pressure sensor 10 to the wrist can be used. That is, the present invention is not limited to the configuration where the air bag is used.

The pressure sensor 10 is configured to input a pressure signal, which is to be detected by each pressure detecting element 12 configuring the element row 120, to the control unit 30.

The control unit 30 includes a ROM (Read Only Memory), a RAM (Random Access Memory) and a processor. The processor executes programs stored in the ROM, so that the control unit collectively controls the entire main body part 1. The programs include a fatigue degree determination program. The RAM functions as a work memory when the control unit 30 executes a variety of processing.

The display unit 50 is to display a variety of information, and is configured by a liquid crystal display device, for example.

The motion detecting sensor 60 is a sensor for detecting body motion of a user, and is configured by one or more sensors selected from an acceleration sensor, an angular velocity sensor, an air pressure sensor and the like.

The operation unit 70 is an interface for operating the biological information measurement device 100, and is configured by buttons, a dial, a touch panel integrated with the display unit 50, and the like, which are provided to the main body part 1.

The storage medium 40 is a medium to and from which data can be stored and read, and is configured by a flash memory and the like, for example. As the storage medium 40, a portable medium such as a memory card may be used or a medium that is fixed to the main body part 1 and cannot be thus taken out may be used.

In the storage medium 40, fatigue degree determination information that is used so as to determine a fatigue degree is stored.

The fatigue degree determination information is information in which a degree of change of one biological heart rate relative to the other biological heart rate of a biological heart rate while a person is awake and at rest and a biological heart rate while the person is sleeping and a fatigue degree (oxidative stress degree) of the person are associated with each other.

The degree of change of the two biological heart rates means a difference value of the two biological heart rates or a ratio of change of one of the two biological heart rates relative to the other, for example.

The difference value of the two biological heart rates is a value obtained by subtracting one biological heart rate of the two biological heart rates from the other biological heart rate.

The ratio of change of the two biological heart rates is a value obtained by dividing the difference value, which is obtained by subtracting one biological heart rate of the two biological heart rates from the other biological heart rate, by the one biological heart rate, or a value obtained by multiplying the value obtained as a result of the division by 100.

The fatigue degree determination information is configured by table data, in which a plurality of combinations of the degree of change of the biological heart rates and the fatigue degree (oxidative stress degree) is registered, a calculation equation expressing a relation between the degree of change of the biological heart rates and the fatigue degree (oxidative stress degree) by a function, or the like.

The inventors verified a relation between a heart rate and an oxidative stress degree (Oxidation Stress Index: OSI) of a person, and found out that a degree of change of one biological heart rate relative to the other biological heart rate of a heart rate while the person is awake and at rest and a heart rate while the person is sleeping and an oxidative stress degree, which is one of indexes of the fatigue degree, have correlation.

Specifically, the inventors set, as the test subjects, 52 healthy males of ages from 30 to 60 who were daytime workers, and measured the heart rates of each test subject during sleep for 7 days by using an electrocardiograph. Also, the inventors gathered blood from each test subject for measuring the oxidative stress degree from A.M. 09:00 to P.M. 13:00 at which each test subject was awake on two days of a day before the measurement start day of the 7 days and a day after the measurement end day. Also, the inventors measured the heart rates by using an upper arm-type sphygmomanometer, together with the blood gathering.

By the measurements, the inventors obtained the heart rates during sleep for 7 days, the heart rates during the awakening and rest for 2 days and the oxidative stress degrees for 2 days, from each of the 52 test subjects.

The inventors calculated and set an average value of the heart rates during sleep, as a night-time heart rate, calculated and set an average value of the heart rates during the awakening and rest, as a daytime heart rate, and calculated and set an average value of the oxidative stress degrees for 2 days, as a fatigue degree, for each test subject.

Figure 4:
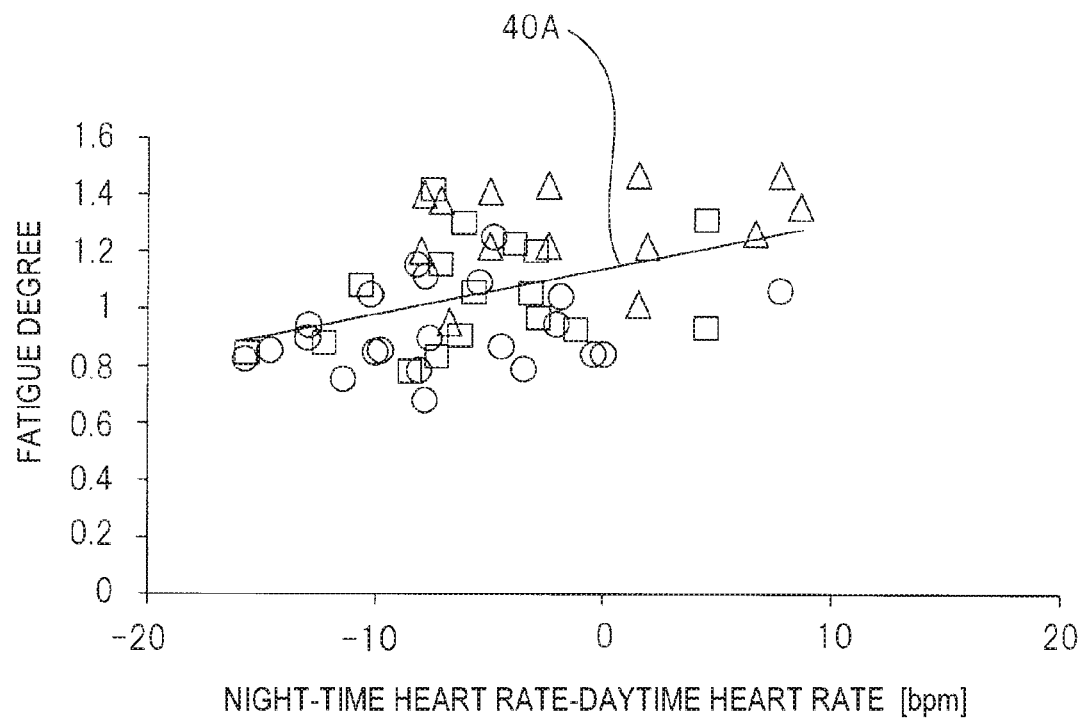
FIG. 4 depicts a verification result of a relation between a heart rate change and an oxidative stress degree.

FIG. 4 depicts a verification result of a relation between the heart rate and the oxidative stress degree.

In a graph of FIG. 4, the horizontal axis indicates a difference value obtained by subtracting the daytime heart rate from the night-time heart rate. In the graph of FIG. 4, the vertical axis indicates the fatigue degree. Also, in the plot data of the graph, "○" indicates data of the test subjects who were 40 years old or younger, "□" indicates data of the test subjects who were from 41 years old to 50 years old, and "Δ" indicates data of the test subjects who were 51 years old or older.

Figure 5:
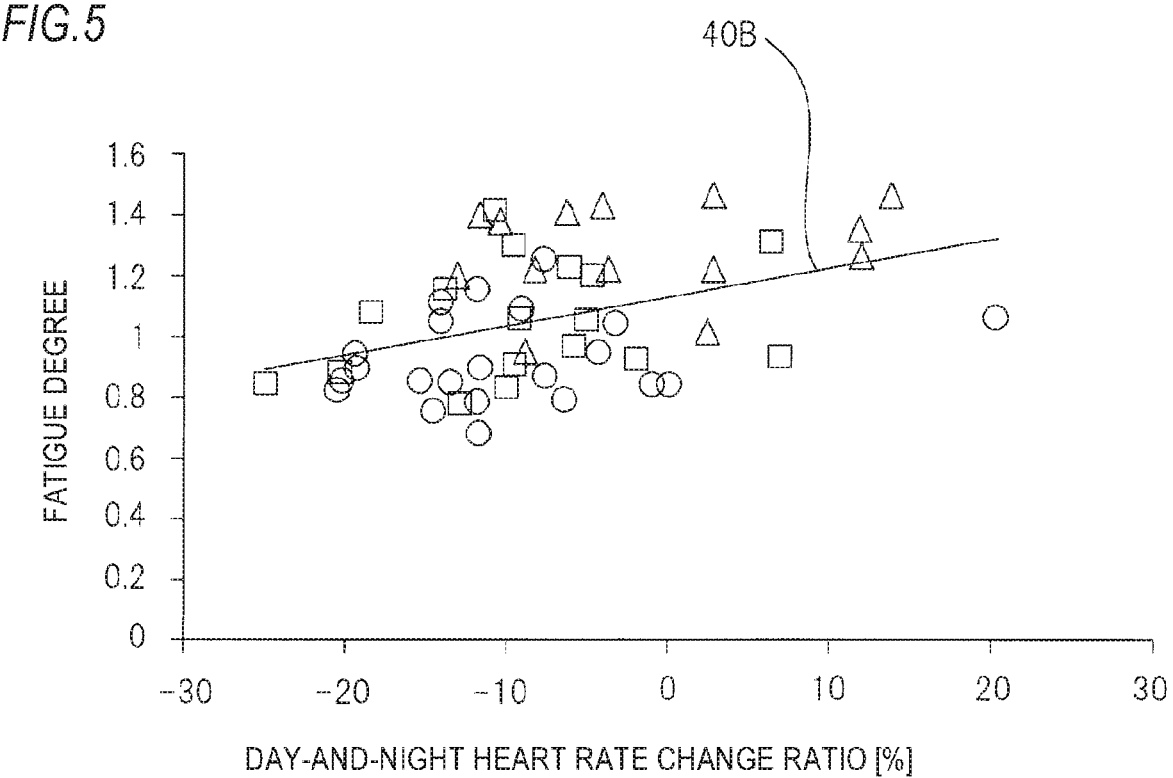
FIG. 5 depicts a verification result of the relation between the heart rate change and an oxidative stress degree.

FIG. 5 depicts a verification result of the relation between the heart rate and the oxidative stress degree.

In a graph of FIG. 5, the values on the horizontal axis indicate normalized data (day-and-night heart rate change ratio [%]) obtained by dividing the difference values, which are obtained by subtracting the daytime heart rates from the night-time heart rates, by the daytime heart rates and then multiplying the resultant values by 100. The others are the same as the graph of FIG. 4.

According to the graphs shown in FIGS. 4 and 5, it can be seen that the greater the ratio of the heart rate during sleep relative to the heart rate during the awakening and rest is, the higher the fatigue degree is, and the smaller the ratio of the heart rate during sleep relative to the heart rate during the awakening and rest is, the lower the fatigue degree is.

In the case of a healthy person, the heart rate during sleep tends to fall below the heart rate during the daytime activity. However, it is thought that when the fatigue is accumulated over a long time, the heart rate is difficult to fall below the heart rate during the daytime due to a spiritual influence, insufficient refreshing sleep and the like. This theory was proved by verifying a relation between the oxidative stress degree measured by the blood gathering and the actually measured heart rate.

In the meantime, as described above, the pulse rate and the heart rate of the healthy person are the same. Therefore, like the heart rate, the pulse rate and the oxidative stress degree also have correlation, as shown in FIGS. 4 and 5.

A function expressing a straight line 40A obtained by the least square method from all the plot data shown in FIG. 4 is expressed by a following equation (1) where the vertical axis is denoted with Y and the horizontal axis is denoted with X.

$$Y=0.016X+1.1462 \tag{1}$$

Also, a function expressing a straight line 40B obtained by the least square method from all the plot data shown in FIG. 5 is expressed by a following equation (2) where the vertical axis is denoted with Y and the horizontal axis is denoted with X.

$$Y=0.0095X+1.1359 \tag{2}$$

In the storage medium 40, information of the equation (1) or the equation (2) is stored as the fatigue degree determination information, for example.

The fatigue degree determination information stored in the storage medium 40 may be stored by a maker during the manufacturing of the biological information measurement device 100 or may be stored by a downloading via a network when the biological information measurement device 100 can connect to the network such as the Internet.

Figure 6:
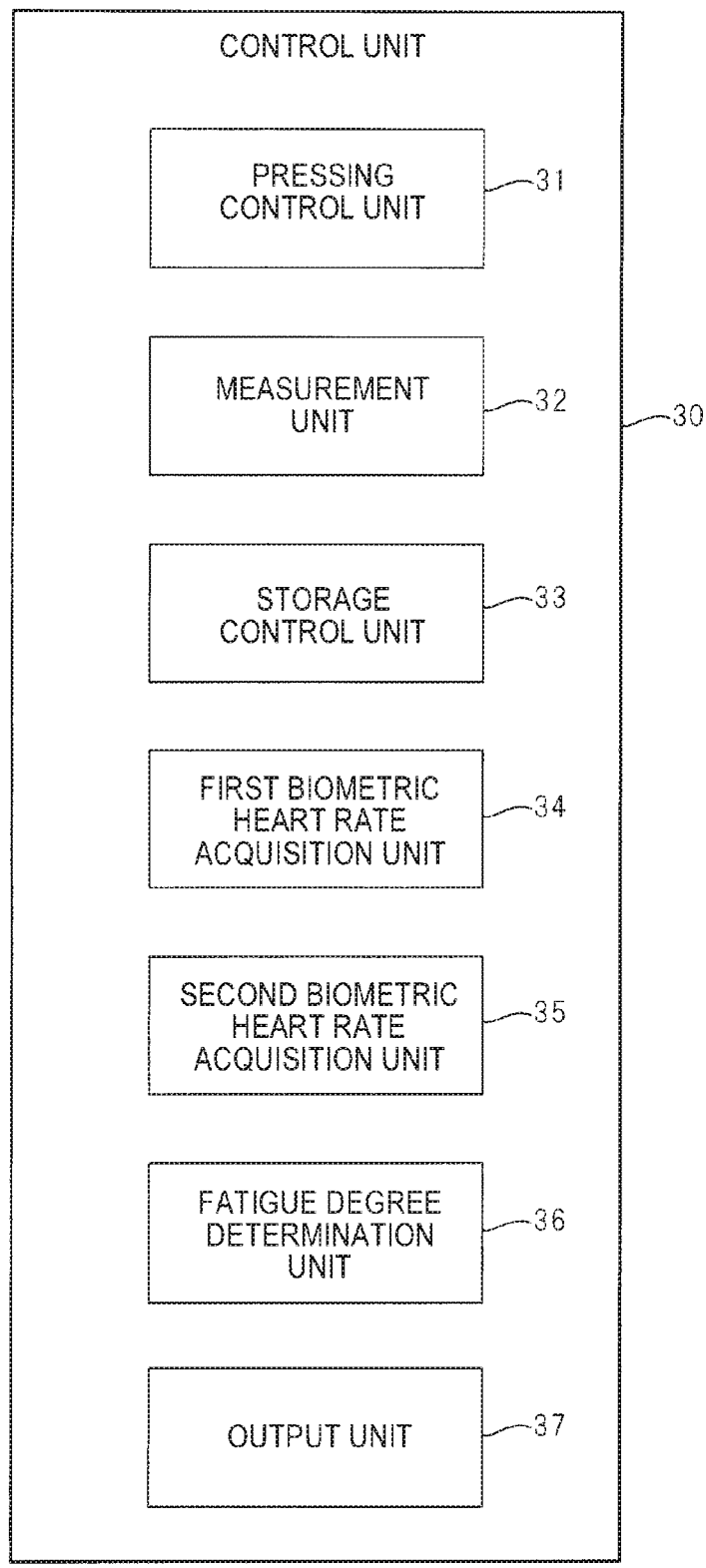
FIG. 6 is a functional block diagram of a control unit 30 shown in FIG. 3.

FIG. 6 is a functional block diagram of the control unit 30 shown in FIG. 3.

The control unit 30 is configured to function as a pressing control unit 31, a measurement unit 32, a storage control unit 33, a first biological heart rate acquisition unit 34, a second biological heart rate acquisition unit 35, a fatigue degree determination unit 36, and an output unit 37 by executing a program stored in the ROM.

The pressing control unit 31 is configured to drive the pressing mechanism 20, thereby controlling a pressing force of the pressure sensor 10 to be applied to the wrist by the pressing mechanism 20.

In a state where the pressure sensor 10 is pressed to the wrist with an optimal pressing force by the pressing mechanism 20, the measurement unit 32 is configured to measure a pulse rate by calculating the pulse rate, which is a biological heart rate of the user wearing the biological information measurement device 100, every one pule or every multiple pulses on the basis of information of a pressure pulse wave detected by an optimal pressure detecting element of the plurality of pressure detecting elements 12 configuring the element row 120.

The optimal pressing force is a pressing force with which it is possible to implement a state, i.e., a tonometry state where it is possible to detect a pressure pulse wave without an influence of a circumferential tension of a blood vessel from the radial artery TD pressed by the optimal pressing force. The optimal pressure detecting element indicates the pressure detecting element 12 positioned immediately above the radial artery TD pressed and flattened due to the pressing of the pressure sensor 10 by the optimal pressing force.

In the biological information measurement device 100, it is possible to set any one of a sleeping mode and an activity mode by the operation unit 70 so as to determine whether an activity state of the user is during sleep or during activity other than the sleep.

In the below, it is assumed that when going to bed, the user operates the operation unit 70 to set the biological information measurement device 100 to the sleeping mode and when getting out of bed, the user operates the operation unit 70 to set the biological information measurement device 100 to the activity mode.

The storage control unit 33 is configured to store, in the storage medium 40, measured data including a pulse rate measured by the measurement unit 32, detection date (which is synonymous with a measurement date of the pulse rate) and detection time of a pressure pulse wave used to calculate the pulse rate, a detection signal of the motion detecting sensor 60 upon the detection of the pressure pulse wave, and mode information indicative of the operation mode (the sleeping mode or the activity mode) set upon the detection of the pressure pulse wave.

The first biological heart rate acquisition unit 34 is configured to generate a first pulse rate, which is a first biological heart rate while the user is awake and at rest, on the basis of the measured data measured from the user by the measurement unit 32 and stored in the storage medium 40, and to store the generated first pulse rate in the RAM, thereby acquiring the first pulse rate.

The second biological heart rate acquisition unit 35 is configured to generate a second pulse rate, which is a second biological heart rate while the user is sleeping, on the basis of the measured data measured from the user by the measurement unit 32 and stored in the storage medium 40, and to store the generated second pulse rate in the RAM, thereby acquiring the second pulse rate.

The fatigue degree determination unit 36 is configured to read out the fatigue degree determination information stored in the storage medium 40 and to store the same in the RAM, and to determine a fatigue degree of the user, based on the fatigue degree determination information, the first pulse rate acquired by the first biological heart rate acquisition unit 34 and the second pulse rate acquired by the second biological heart rate acquisition unit 35. The fatigue degree to be here determined is an estimated value of the oxidative stress degree of the user.

Specifically, when the fatigue degree determination information stored in the storage medium 40 is the equation (1), the fatigue degree determination unit 36 subtracts the first pulse rate from the second pulse rate, and substitutes a difference value obtained by the subtraction in "X" of the equation (1), thereby calculating the fatigue degree.

Also, when the fatigue degree determination information stored in the storage medium 40 is the equation (2), the fatigue degree determination unit 36 subtracts the first pulse rate from the second pulse rate, divides a difference value obtained by the subtraction by the first pulse rate, multiplies a resultant value thereof by 100 and substitutes a value obtained by the multiplication in "X" of the equation (2), thereby calculating the fatigue degree.

The output unit 37 is configured to output information of the fatigue degree determined by the fatigue degree determination unit 36 to the display unit 50, thereby displaying the information on the display unit 50.

Meanwhile, in a configuration where the biological information measurement device 100 includes a speaker configured to output a sound, the output unit 37 may be configured to output the information of the fatigue degree determined by the fatigue degree determination unit 36 to the speaker, thereby notifying the user of the fatigue degree.

In the biological information measurement device 100 configured as described above, when the user pushes a measurement start button in a state where one of the sleeping mode and the activity mode is set, the pulse rate is periodically measured from the user, and the measured data including the measured pulse rate, the detection date and detection time of the pressure pulse wave used to calculate the pulse rate, the motion detection signal upon the detection of the pressure pulse wave, and the mode information indicative of the set operation mode is sequentially stored in the storage medium 40.

At any timing, when the user operates the operation unit 70 to issue a determination instruction of the fatigue degree, the determination instruction is input to the control unit 30, so that the control unit 30 determines the fatigue degree and displays the determined fatigue degree on the display unit 50.

When the determination instruction is input, the first biological heart rate acquisition unit 34 sets, as a determination time period, a time period from date and time at which the determination instruction is issued to time before predetermined time.

As the determination time period, it is preferably to set a time period in which the measured data including the mode information of the sleeping mode and the measured data including the mode information of the activity mode are to be obtained all the time. For example, 24 hours are set. However, the present invention is not limited thereto.

Then, the first biological heart rate acquisition unit 34 is configured to extract the measured data, which includes the detection date and detection time of the determination time period, from the storage medium 40, and to further extract the measured data during activity, which includes the mode information indicative of the activity mode, of the extracted measured data. The measured data during activity to be here extracted includes the information of the pulse rate while the user is awake.

Then, the first biological heart rate acquisition unit 34 is configured to analyze the detection signal of the motion detecting sensor 60 included in the measured data during activity and to specify measured data during rest in which the motion of the user is equal to or less than a threshold value. The measured data during rest to be here specified includes the information of the pulse rate while the user is awake and at rest.

Finally, the first biological heart rate acquisition unit 34 is configured to calculate a representative value of the pulse rates included in the measured data during rest and to store the calculated representative value in the RAM, as the first pulse rate, thereby acquiring the first pulse rate.

Here, the representative value of the plurality of pulse rates is a value indicative of an entire tendency of the plurality of pulse rates such as an average value of the plurality of pulse rates, an average value of the pulse rates, from which the maximum and minimum values are excluded, of the plurality of pulse rates, a modal value of the plurality of pulse rates, an intermediate value of the plurality of pulse rates or the like Also, the second biological heart rate acquisition unit 35 is configured to extract, from the storage medium 40, the measured data including the detection date and detection time of the determination time period, and to extract the night-time measured data, which includes the mode information of the sleeping mode, of the extracted measured data.

Then, the second biological heart rate acquisition unit 35 is configured to analyze the detection signal of the motion detecting sensor 60, which is included in each of the extracted night-time measured data, and to specify measured data during sleep, which includes a detection signal with which it is possible to determine that the user is sleeping. The measured data during sleep to be here specified includes the information of the pulse rate while the user is sleeping.

Finally, the second biological heart rate acquisition unit 35 is configured to calculate a representative value of the pulse rates included in each of the specified measured data during sleep by the above-described method or the like, and to store the calculated representative value in the RAM, as the second pulse rate, thereby acquiring the second pulse rate.

When the first pulse rate and the second pulse rate are stored in the RAM, the fatigue degree determination unit 36 reads out the fatigue degree determination information from the storage medium 40 and stores the same in the RAM, determines a fatigue degree on the basis of the first pulse rate, the second pulse rate and the fatigue degree determination information, and displays the determined fatigue degree on the display unit 50.

For example, when the determination instruction of the fatigue degree is issued at A.M. 10:00, July 14, the representative value of the pulse rates while the user is sleeping from A.M. 10:00, July 13 to A.M. 10:00, July 14 is stored as the second pulse rate in the RAM, and the representative value of the pulse rates while the user is awake and at rest from A.M. 10:00, July 13 to A.M. 10:00, July 14 is stored as the first pulse rate in the RAM. Then, the fatigue degree is determined on the basis of the first pulse rate, the second pulse rate and the fatigue degree determination and is displayed on the display unit 50.

In this way, according to the biological information measurement device 100, since the fatigue degree (estimated value of the oxidative stress degree) of the user is determined on the basis of the first pulse rate while the user is awake and at rest, the second pulse rate while the user is sleeping and the fatigue degree determination information experimentally obtained and stored in advance in the storage medium 40, it is possible to determine the fatigue degree without executing the complex calculation processing. Therefore, it is possible to reduce the processing load of the control unit 30.

Also, for determination of the fatigue degree, the first pulse rate and the second pulse rate are required. However, the first pulse rate can be easily obtained by measuring the pulse rate at least one time in a state where the user takes a rest in the daytime. Therefore, the user does not have to continuously wear the biological information measurement device 100 in the daytime, so that it is possible to reduce a burden of the user.

When the biological information measurement device 100 is a battery-driven type, it is thought that the charging is frequently performed except while the user is sleeping. While the device is being charged, the pulse rate cannot be measured. For this reason, with the configuration where the pulse rate has only to be measured at least one time in the daytime, it is possible to accurately determine the fatigue degree and to cope with the charging of the device.

In the below, modified embodiments of the biological information measurement device 100 are described.

First Modified Embodiment

The first biological heart rate acquisition unit 34, the second biological heart rate acquisition unit 35 and the fatigue degree determination unit 36 may be configured to operate at predetermined timing to determine the fatigue degree as well as to operate in response to the determination instruction from the user.

The timing includes a timing at which the operation mode is switched from the sleeping mode to the activity mode, a timing at which the operation mode is switched from the activity mode to the sleeping mode, a timing at which the power supply of the biological information measurement device 100 becomes on, and the like.

At the timings, the user is operating the biological information measurement device 100. For this reason, when the fatigue degree is displayed on the display unit 50 or is output from the speaker at the timings, it is possible to naturally notify the user of the fatigue degree.

Also, it is assumed that the operation mode is switched every day by the user. For this reason, when the fatigue degree is notified at the timing at which the operation mode is switched, the user can know the daily subtle changes of the fatigue degree and utilize the same for improvement of living and the like.

Second Modified Embodiment

In the above illustrative embodiment, the first biological heart rate acquisition unit 34 is configured to extract the measured data, which includes the detection date and detection time of the determination time period, from the storage medium 40, and to extract the measured data during activity from the extracted measured data, based on the mode information.

In a second modified embodiment, the first biological heart rate acquisition unit 34 is configured to analyze the detection signals included in the measured data extracted from the storage medium 40 without using the mode information indicative of the activity mode, and to distinguish between the signal measured during sleep and the signal measured during the activity other than the sleep, thereby extracting the measured data during activity.

Also, in the second modified embodiment, the second biological heart rate acquisition unit 35 is configured to analyze the detection signals included in the measured data extracted from the storage medium 40 without using the mode information indicative of the sleeping mode, and to distinguish between the signal measured during sleep and the signal measured during the activity other than the sleep, thereby extracting the night-time measured data.

According to the second modified embodiment, since the information of the operation mode is not used so as to acquire the first pulse rate and the second pulse rate, it is not necessary for the user to set the operation mode. Therefore, it is not necessary to worry about forgetting the switching of the operation mode, so that it is possible to improve the usability of the biological information measurement device 100.

Third Modified Embodiment

The second biological heart rate acquisition unit 35 may be configured to specify measured data, which can be determined as being measured during non-REM sleep from the detection signals of the motion detecting sensor 60, of each of the specified measured data during sleep, and to set a representative value of the pulse rates included in the measured data, as the second pulse rate. Since it is thought that the pulse rate reduces during non-REM sleep, when the pulse rate during non-REM sleep is acquired as the second pulse rate and is used for determination of the fatigue degree, it is possible to improve the determination accuracy of the fatigue degree.

Fourth Modified Embodiment

The second biological heart rate acquisition unit 35 may be configured to acquire, as the second pulse rate, the minimum pulse rate of the pulse rates included in each of the specified measured data during sleep. A possibility that the minimum pulse rate during sleep is a pulse rate in the non-REM sleep state is high. Since it is thought that the pulse rate reduces during non-REM sleep, when the pulse rate during non-REM sleep is acquired as the second pulse rate and is used for determination of the fatigue degree, it is possible to improve the determination accuracy of the fatigue degree.

Fifth Modified Embodiment

Figure 7:
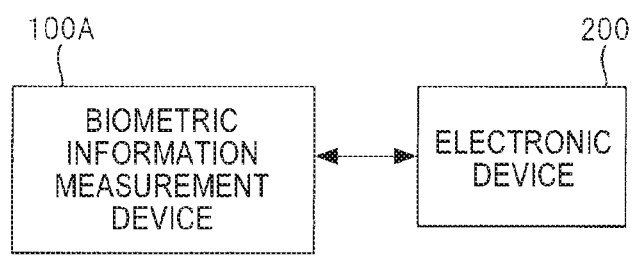
FIG. 7 depicts a schematic configuration of a fatigue degree determination system in accordance with an illustrative embodiment of the present invention.

FIG. 7 depicts a schematic configuration of a fatigue degree determination system in accordance with an illustrative embodiment of the present invention. The fatigue degree determination system shown in FIG. 7 includes a biological information measurement device 100A and an electronic device 200.

Since an internal hardware configuration of the biological information measurement device 100A is the same as the biological information measurement device 100 except that a communication interface for performing communication with the electronic device 200 is added, the descriptions thereof are omitted.

In a functional block diagram of the control unit 30 of the biological information measurement device 100A, the first biological heart rate acquisition unit 34, the second biological heart rate acquisition unit 35, the fatigue degree determination unit 36 and the output unit 37 of FIG. 6 are omitted.

The electronic device 200 is an electronic device such as a personal computer, a smart phone, a table terminal or the like.

The electronic device 200 can be connected to the biological information measurement device 100A in a wired or wireless manner, and can read the data in the storage medium 40 of the biological information measurement device 100A.

In the meantime, when the storage medium 40 of the biological information measurement device 100A is a portable type, the electronic device 200 has a means capable of reading the data from the storage medium, and may be configured to read the data from the mounted storage medium.

In the fatigue degree determination system of FIG. 7, it is presumed that the user of the biological information measurement device 100A installs an application (fatigue degree determination application) for determining the fatigue degree in the electronic device 200 carried by the user. The fatigue degree determination application includes the fatigue degree determination program.

Figure 8:
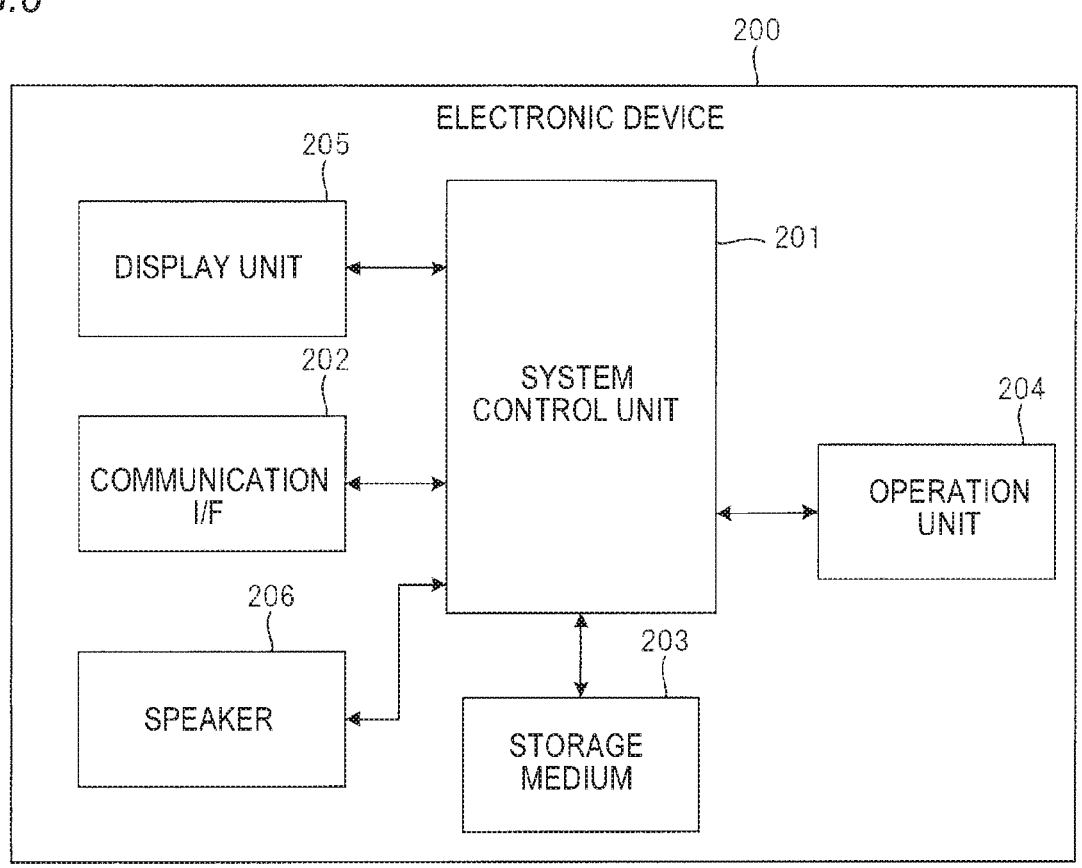
FIG. 8 depicts an internal hardware configuration of an electronic device 200 shown in FIG. 7.

FIG. 8 depicts an internal hardware configuration of the electronic device 200 of the fatigue degree determination system shown in FIG. 7.

The electronic device 200 includes a system control unit 201 configured to collectively control the entire device, a communication interface (I/F) 202, a storage medium 203, an operation unit 204, a display unit 205, and a speaker 206.

The system control unit 201 includes a processor, a ROM in which a program and the like to be executed by the processor are stored, and a RAM as a work memory. In the ROM, the fatigue degree determination application is stored.

The communication OF 202 is an interface for wired or wireless connection with an electronic device including the biological information measurement device 100A.

In the storage medium 203, the measured data read out from the biological information measurement device 100A is stored. The storage medium 203 is configured by a flash memory and the like, for example. The storage medium 203 may be detachably mounted to the electronic device 200.

In the storage medium 203, the fatigue degree determination information is stored upon the install of the fatigue degree determination application.

The operation unit 204 is an interface for inputting an instruction signal to the system control unit 201, and is configured by a keyboard, a mouse, a button, a touch panel or the like.

The display unit 205 is to display a variety of information and is configured by a liquid crystal display device or the like, for example.

Figure 9:
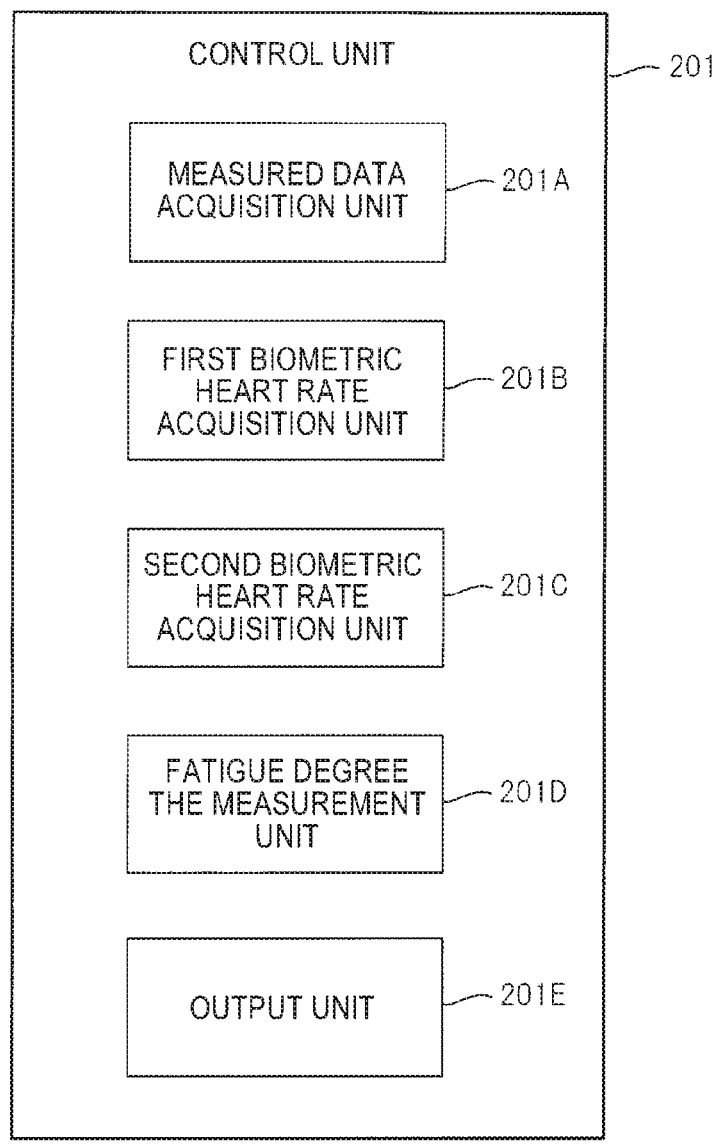
FIG. 9 is a functional block diagram of a system control unit 201 of the electronic device 200 shown in FIG. 7.

FIG. 9 is a functional block diagram of the system control unit 201 of the electronic device 200 shown in FIG. 8.

As the processor executes the fatigue degree determination program, the system control unit 201 functions as a measured data acquisition unit 201A, a first biological heart rate acquisition unit 201B, a second biological heart rate acquisition unit 201C, a fatigue degree determination unit 201D and an output unit 201E. The system control unit 201 functions as a fatigue degree determination device.

The measured data acquisition unit 201A is configured to acquire the measured data stored in the storage medium 40 from the storage medium 40 of the biological information measurement device 100A and to store the same in the storage medium 203.

The first biological heart rate acquisition unit 201B has the same function as the first biological heart rate acquisition unit 34, except that a reading destination of the measured data is the storage medium 203.

The second biological heart rate acquisition unit 201C has the same function as the second biological heart rate acquisition unit 35, except that a reading destination of the measured data is the storage medium 203.

The fatigue degree determination unit 201D has the same function as the fatigue degree determination unit 36, except that a reading destination of the fatigue degree determination information is the storage medium 203.

The output unit 201E has the same function as the output unit 37, except that an output destination of the information of the fatigue degree is the display unit 205 or the speaker 206.

In the fatigue degree determination system configured as described above, the user of the biological information measurement device 100A activates the fatigue degree application installed in the electronic device 200 carried by the user, thereby issuing a determination instruction of the fatigue degree to the system control unit 201. The system control unit 201 having received the determination instruction is configured to set, as the determination time period, a time period from date and time, at which the determination instruction is issued, to time before the predetermined time (for example, 24 hours).

Then, the first biological heart rate acquisition unit 201B is configured to acquire the first pulse rate while the user is awake and at rest, based on the measured data including the detection date and detection time of the determination time period. Also, the second biological heart rate acquisition unit 201C is configured to acquire the second pulse rate while the user is sleeping, based on the measured data including the detection date and detection time of the determination time period.

Then, the fatigue degree determination unit 201D is configured to read out the fatigue degree determination information from the storage medium 203 and to store the same in the RAM, to determine the fatigue degree on the basis of the first pulse rate, the second pulse rate and the fatigue degree determination information and to display the determined fatigue degree on the display unit 205.

In this way, it is possible to determine the fatigue degree in the electronic device 200, which can perform communication with the biological information measurement device 100A capable of measuring the pulse rate, and to notify the fatigue degree to the user.

According to the above configuration, it is possible to reduce an amount of the processing in the biological information measurement device 100A and to prolong the battery lifetime of the device. Also, even when the biological information measurement device 100A is not provided with the display unit, the speaker or the like, it is possible to notify the user of the fatigue degree, so that it is also possible to facilitate the miniaturization and cost saving of the biological information measurement device 100A.

In the above, the biological information measurement device 100 and the biological information measurement device 100A are configured to measure the pulse rate on the basis of the pressure pulse wave detected by the pressure sensor 10. However, the measurement method of the pulse rate or the measurement frequency of the pulse rate is not limited thereto. For example, the biological information measurement device 100 and the biological information measurement device 100A may be configured to measure the pulse rate on the basis of the pulse wave detected by a photoelectric pulse wave sensor.

Also, the biological information measurement device 100; 100A may be configured to measure and store the pulse rate with preset time intervals such as every 30 minutes or every one hour.

In the fifth modified embodiment, the electronic device 200 is configured to determine the fatigue degree. However, the fatigue degree may be determined by a server capable of performing communication with the electronic device 200 and the determined fatigue degree may be replied from the server to the electronic device 200, so that the fatigue degree may be checked with the electronic device 200. In this case, the server functions as the fatigue degree determination device.

Also, the biological information measurement device 100; 100A may be configured to measure and store the heart rate, as the biological heart rate, every one pule, every multiple pulses or with preset time intervals such as every 30 minutes or every one hour every 30 minutes by using an electrocardiographic sensor and the like.

Also, the biological information measurement device 100; 100A may have functions of measuring and storing blood pressure information, in addition to the biological heart rate such as the pulse rate or the heart rate.

The disclosed illustrative embodiments are exemplary in every respect and should not be construed as being limited. The scope of the present invention is defined in the claims, not in the above description, and includes all changes within the meaning and scope equivalent to the claims.

As described above, the specification discloses following items.

(1) A fatigue degree determination device including a first biological heart rate acquisition unit configured to acquire a first biological heart rate while a user is awake and at rest, based on a biological heart rate measured from the user, a second biological heart rate acquisition unit configured to acquire a second biological heart rate while the user is sleeping, based on the biological heart rate measured from the user, and a fatigue degree determination unit configured to determine a fatigue degree of the user, based on information read out from a storage medium and the first biological heart rate and second biological heart rate, the storage medium storing the information in which a degree of change of one biological heart rate relative to the other biological heart rate of a biological heart rate while a person is awake and at rest and a biological heart rate while the person is sleeping and a fatigue degree are associated with each other.

(2) The fatigue degree determination device according to the above (1), wherein the fatigue degree determination unit is configured to calculate a degree of change of one relative to the other of the first biological heart rate and the second biological heart rate and to determine a fatigue degree, which corresponds to the degree of change in the information, as the fatigue degree of the user.

(3) The fatigue degree determination device according to the above (1) or (2), wherein the fatigue degree included in the information is an oxidative stress degree.

(4) The fatigue degree determination device according to one of the above (1) to (3), wherein the first biological heart rate acquisition unit is configured to acquire the first biological heart rate on the basis of a biological heart rate measured from the user for a determination time period from a timing, at which the fatigue degree determination unit determines the fatigue degree of the user, to time before predetermined time, and wherein the second biological heart rate acquisition unit is configured to acquire the second biological heart rate on the basis of the biological heart rate measured from the user for the determination time period.

(5) The fatigue degree determination device according to the above (4), wherein the predetermined time is 24 hours.

(6) The fatigue degree determination device according to one of the above (1) to (5), further including an output unit configured to output information of the fatigue degree of the user determined by the fatigue degree determination unit to a display unit or a speaker, wherein the fatigue degree determination unit is configured to determine the fatigue degree of the user at predetermined timing.

(7) The fatigue degree determination device according to one of the above (1) to (6), wherein the degree of change is a difference value obtained by subtracting the one biological heart rate from the other biological heart rate, and wherein the fatigue degree determination unit is configured to subtract one of the first biological heart rate and the second biological heart rate from the other and to determine a fatigue degree, which corresponds to a value obtained as a result of the subtraction in the information, as the fatigue degree of the user.

(8) The fatigue degree determination device according to one of the above (1) to (6), wherein the degree of change is a value obtained by dividing a difference value, which is obtained by subtracting the one biological heart rate from the other biological heart rate, by the one biological heart rate or a value obtained by multiplying the value obtained as a result of the division by 100, and wherein the fatigue degree determination unit is configured to calculate a ratio of change of the biological heart rate of the user by dividing a difference value, which is obtained by subtracting one of the first biological heart rate and the second biological heart rate from the other, by the one or by dividing a difference value, which is obtained by subtracting one of the first biological heart rate and the second biological heart rate from the other, by the one and multiplying the value obtained as a result of the division by 100, and to determine a fatigue degree, which corresponds to the ratio of change in the information, as the fatigue degree of the user.

(9) A biological information measurement device including the fatigue degree determination device according to one of the above (1) to (8) and a measurement unit configured to measure a biological heart rate from the user, wherein the first biological heart rate acquisition unit is configured to acquire the first biological heart rate by generating the first biological heart rate from the biological heart rate measured by the measurement unit, and wherein the second biological heart rate acquisition unit is configured to acquire the second biological heart rate by generating the second biological heart rate from the biological heart rate measured by the measurement unit.

(10) A fatigue degree determination method including a first biological heart rate acquisition step of acquiring a first biological heart rate while a user is awake and at rest, based on a biological heart rate measured from the user, a second biological heart rate acquisition step of acquiring a second biological heart rate while the user is sleeping, based on the biological heart rate measured from the user, and a fatigue degree determination step of determining a fatigue degree of the user, based on information read out from a storage medium and the first biological heart rate and second biological heart rate, the storage medium storing the information in which a degree of change of one biological heart rate relative to the other biological heart rate of a biological heart rate while a person is awake and at rest and a biological heart rate while the person is sleeping and a fatigue degree are associated with each other.

(11) A fatigue degree determination program configured to enable a computer to execute a first biological heart rate acquisition step of acquiring a first biological heart rate while a user is awake and at rest, based on a biological heart rate measured from the user, a second biological heart rate acquisition step of acquiring a second biological heart rate while the user is sleeping, based on the biological heart rate measured from the user, and a fatigue degree determination step of determining a fatigue degree of the user, based on information read out from a storage medium and the first biological heart rate and second biological heart rate, the storage medium storing the information in which a degree of change of one biological heart rate relative to the other biological heart rate of a biological heart rate while a person is awake and at rest and a biological heart rate while the person is sleeping and a fatigue degree are associated with each other.

According to the present invention, it is possible to provide the fatigue degree determination device, the fatigue degree determination method, the fatigue degree determination program and the biological information measurement device capable of accurately obtaining the fatigue degree under light load.

Although the present invention has been described with reference to the specific illustrative embodiments, the present invention is not limited to the illustrative embodiments and can be diversely changed without departing from the disclosed technical spirit of the present invention.

What is claimed is:

1. A fatigue degree determination device comprising:
a first biological heart rate acquisition unit configured to acquire a first biological heart rate while a user is awake and at rest, based on a biological heart rate measured from the user;
a second biological heart rate acquisition unit configured to acquire a second biological heart rate while the user is sleeping, based on the biological heart rate measured from the user, and
a fatigue degree determination unit configured to determine a fatigue degree of the user, based on information read out from a storage medium, the first biological heart rate and the second biological heart rate, the storage medium storing the information in which a degree of change of one biological heart rate relative to the other biological heart rate of a biological heart rate while a person is awake and at rest and a biological heart rate while the person is sleeping and a fatigue degree are associated with each other.

2. The fatigue degree determination device according to claim 1, wherein the fatigue degree determination unit is configured to calculate a degree of change of one relative to the other of the first biological heart rate and the second biological heart rate and to determine a fatigue degree, which corresponds to the degree of change in the information, as the fatigue degree of the user.

3. The fatigue degree determination device according to claim 1, wherein the fatigue degree included in the information is an oxidative stress degree.

4. The fatigue degree determination device according to claim 1, wherein the first biological heart rate acquisition unit is configured to acquire the first biological heart rate on the basis of a biological heart rate measured from the user for a determination time period from a timing, at which the fatigue degree determination unit determines the fatigue degree of the user, to time before predetermined time, and
   wherein the second biological heart rate acquisition unit is configured to acquire the second biological heart rate on the basis of the biological heart rate measured from the user for the determination time period.

5. The fatigue degree determination device according to claim 4, wherein the predetermined time is 24 hours.

6. The fatigue degree determination device according to claim 1, further comprising an output unit configured to output information of the fatigue degree of the user determined by the fatigue degree determination unit to a display unit or a speaker,
   wherein the fatigue degree determination unit is configured to determine the fatigue degree of the user at predetermined timing.

7. The fatigue degree determination device according to claim 1, wherein the degree of change is a difference value obtained by subtracting the one biological heart rate from the other biological heart rate, and
   wherein the fatigue degree determination unit is configured to subtract one of the first biological heart rate and the second biological heart rate from the other and to determine a fatigue degree, which corresponds to a value obtained as a result of the subtraction in the information, as the fatigue degree of the user.

8. The fatigue degree determination device according to claim 1, wherein the degree of change is a value obtained by dividing a difference value, which is obtained by subtracting the one biological heart rate from the other biological heart rate, by the one biological heart rate or a value obtained by multiplying the value obtained as a result of the division by 100, and
   wherein the fatigue degree determination unit is configured to calculate a ratio of change of the biological heart rate of the user by dividing a difference value, which is obtained by subtracting one of the first biological heart rate and the second biological heart rate from the other, by the one or by dividing a difference value, which is obtained by subtracting one of the first biological heart rate and the second biological heart rate from the other, by the one and multiplying the value obtained as a result of the division by 100, and to determine a fatigue degree, which corresponds to the ratio of change in the information, as the fatigue degree of the user.

9. A biological information measurement device comprising:
   the fatigue degree determination device according to claim 1, and
   a measurement unit configured to measure a biological heart rate from the user,
   wherein the first biological heart rate acquisition unit is configured to acquire the first biological heart rate by generating the first biological heart rate from the biological heart rate measured by the measurement unit, and
   wherein the second biological heart rate acquisition unit is configured to acquire the second biological heart rate by generating the second biological heart rate from the biological heart rate measured by the measurement unit.

10. A fatigue degree determination method comprising:
    a first biological heart rate acquisition step of acquiring a first biological heart rate while a user is awake and at rest, based on a biological heart rate measured from the user;
    a second biological heart rate acquisition step of acquiring a second biological heart rate while the user is sleeping, based on the biological heart rate measured from the user, and
    a fatigue degree determination step of determining a fatigue degree of the user, based on information read out from a storage medium, the first biological heart rate and the second biological heart rate, the storage medium storing the information in which a degree of change of one biological heart rate relative to the other biological heart rate of a biological heart rate while a person is awake and at rest and a biological heart rate while the person is sleeping and a fatigue degree are associated with each other.

11. A non-transitory computer-readable storage medium, which stores a fatigue degree determination program configured to enable a computer to execute:
    a first biological heart rate acquisition step of acquiring a first biological heart rate while a user is awake and at rest, based on a biological heart rate measured from the user;
    a second biological heart rate acquisition step of acquiring a second biological heart rate while the user is sleeping, based on the biological heart rate measured from the user, and
    a fatigue degree determination step of determining a fatigue degree of the user, based on information read out from a storage medium, the first biological heart rate and the second biological heart rate, the storage medium storing the information in which a degree of change of one biological heart rate relative to the other biological heart rate of a biological heart rate while a person is awake and at rest and a biological heart rate while the person is sleeping and a fatigue degree are associated with each other.

* * * * *